United States Patent
Smith et al.

(12) 
(10) Patent No.: US 6,187,751 B1
(45) Date of Patent: Feb. 13, 2001

(54) BIOLOGICALLY ACTIVE PEPTIDE OF OB PROTEIN

(75) Inventors: Richard Anthony Godwin Smith, Horseheath; Lee James Beeley, Dorking, both of (GB)

(73) Assignee: SmithKline Beecham p.l.c. (GB)

( * ) Notice: Under 35 U.S.C. 154(b), the term of this patent shall be extended for 0 days.

(21) Appl. No.: 09/391,799

(22) Filed: Sep. 9, 1999

Related U.S. Application Data

(63) Continuation of application No. 08/945,902, filed as application No. PCT/GB96/01094 on May 7, 1996, now abandoned.

(30) Foreign Application Priority Data

May 5, 1995 (GB) .................................. 9509164

(51) Int. Cl.[7] .......................... A61K 38/10; A61K 38/17; C07K 7/08; C07K 14/47; C12N 15/09
(52) U.S. Cl. ............................ 514/12; 435/69.4; 514/13; 514/14; 530/324; 530/326; 530/327; 530/345; 530/410
(58) Field of Search .................... 530/300, 324, 530/326, 345, 350, 399, 410, 327; 514/2, 12.13, 14.21; 435/69.1, 69.4, 69.7

(56) References Cited

U.S. PATENT DOCUMENTS 5,559,208  9/1996  Basinski et al. ................ 530/317
5,968,779 * 10/1999  Campfield et al. .............. 435/69.4

FOREIGN PATENT DOCUMENTS

96/05309  2/1996  (WO) ................ C12N/15/12
96/23514  8/1996  (WO) ................ A61K/38/00
96/23815  8/1996  (WO) ................ C07K/16/18

OTHER PUBLICATIONS

Zhang et al., "Positional Cloning of the Mouse Obese Gene and its Human Homologue", *Nature,* vol. 371, pp. 425–432 (1994).

M. Dayhoff, *Protein Sequence and Structure,* vol. 5, p. 96 (1972).

* cited by examiner

*Primary Examiner*—Jeffrey E. Russel
(74) *Attorney, Agent, or Firm*—Kirk Baumeister; William T. King

(57) ABSTRACT

The present invention provides a protein fragment of the ob protein, being an active site of the protein. The active site is suitably provided by the ob protein when it is in the form of a four helix bundle structure, particularly that having an up-up down-down topology. In particular, the active site is formed from one or more amino acids selected from one or more of the four helices forming the secondary stucture of the ob protein, especially a protein fragment consisting of amino acid residues 26 to 39, 74 to 88, 93 to 113 or 142 to 161. The compounds of the invention arc considered to be capable of regulating the physiological activity of the ob protein and are therefor of potential use in the treatment of nutritional and metabollic disorders, particularly obesity and diabetes in the case of agonists and anorexia and cachexia in the case of antagonists.

17 Claims, No Drawings

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 18 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:1:

Ala Lys Val Gln Asp Asp Thr Lys Thr Leu Ile Lys Thr Ile Val Thr
1               5                  10                  15

Arg Ile (2) INFORMATION FOR SEQ ID NO:2:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:2:

Ser Lys Met Asp Thr Leu Ala Val Tyr Gln Gln Ile Leu Thr
1               5                  10

(2) INFORMATION FOR SEQ ID NO:3:

(i) SEQUENCE CHARACTERISTICS:
       (A) LENGTH: 23 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:3:

Asn Val Ile Gln Ile Ser Asn Asp Leu Glu Asn Leu Arg Asp Leu Leu
1               5                  10                  15

His Val Leu Ala Phe Ser Lys
            20

(2) INFORMATION FOR SEQ ID NO:4:

(i) SEQUENCE CHARACTERISTICS:
       (A) LENGTH: 21 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO:4:

Thr Glu Val Val Ala Leu Ser Arg Leu Leu Gln Gly Ser Leu Gln Asp
1               5                  10                  15

Met Leu Trp Gln Leu
            20

(2) INFORMATION FOR SEQ ID NO:5:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Residue 1 acylated
        (A) NAME/KEY: Other
        (B) LOCATION: 22...22
        (D) OTHER INFORMATION: Disulfide linkage to SEQ ID NO: 6

(xi) SEQUENCE DESCRIPTION: SEQ ID NO:5:

```
Ala Lys Val Gln Asp Asp Thr Lys Thr Leu Ile Lys Thr Ile Val Thr
 1               5                  10                  15

Arg Ile Gly Gly Pro Cys Gly Ser Gly Thr Glu Val Val Ala Leu Ser
            20                  25                  30

Arg Leu Leu Gln Gly Ser Leu Gln Asp Met Leu Trp Gln Leu
        35                  40                  45
```

(2) INFORMATION FOR SEQ ID NO:6:

(i) SEQUENCE CHARACTERISTICS:
        (A) LENGTH: 47 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Residue 1 acylated
        (A) NAME/KEY: Other
        (B) LOCATION: 22...22
        (D) OTHER INFORMATION: Disulfide linkage to SEQ ID NO: 5

(xi) SEQUENCE DESCRIPTION: SEQ ID NO:6:

```
Ala Ser Lys Met Asp Gln Thr Leu Ala Val Tyr Gln Gln Ile Leu Thr
 1               5                  10                  15

Gly Ser Ala Ala Pro Cys Gly Gly Asn Val Ile Gln Ile Ser Asn Asp
            20                  25                  30

Leu Glu Asn Leu Arg Asp Leu Leu His Val Leu Ala Phe Ser Lys
        35                  40                  45
```

(2) INFORMATION FOR SEQ ID NO:7:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Residue 1 methoxy pegylated
        (A) NAME/KEY: Other
        (B) LOCATION: 29...29
        (D) OTHER INFORMATION: Disulfide linkage to SEQ ID NO: 8

```
    (xi) SEQUENCE DESCRIPTION: SEQ ID NO:7:

Ala Lys Asn Val Ile Gln Ile Ser Asn Asp Leu Glu Asn Leu Arg Asp
1               5                   10                  15

Leu Leu His Val Leu Ala Phe Ser Lys Ala Ala Pro Cys
            20                  25

(2) INFORMATION FOR SEQ ID NO:8:

(i) SEQUENCE CHARACTERISTICS:
        (A) LENGTH: 46 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Other
        (B) LOCATION: 1...1
        (D) OTHER INFORMATION: Residue 1 methoxy pegylated
        (A) NAME/KEY: Other
        (B) LOCATION: 22...22
        (D) OTHER INFORMATION: Disulfide linkage to SEQ ID NO: 7

(xi) SEQUENCE DESCRIPTION: SEQ ID NO:8:

Ala Lys Val Gln Asp Asp Thr Lys Thr Leu Ile Lys Thr Ile Val Thr
1               5                   10                  15

Arg Ile Ala Ala Pro Cys Gly Gly Ser Thr Glu Val Val Ala Leu Ser
            20                  25                  30

Arg Leu Leu Gln Gly Ser Leu Gln Asp Met Leu Trp Gln Leu
        35                  40                  45
```

BIOLOGICALLY ACTIVE PEPTIDE OF OB PROTEIN

CROSS REFERENCE TO RELATED APPLICATIONS

This application is a continuation of application U.S. Ser. No. 08/945,902, filed Jan. 28, 1998 now abandoned which is the 35 USC §371 National Stage entry of PCT International Application No. PCT/GB96/01094, filed May 7, 1996.

The invention relates to novel compounds, in particular novel proteins, to compositions containing such compounds and to the use of such compounds in medicine.

The mechanism of the physiological regulation of energy balance in the body—food intake verses energy output—has been the subject of debate for many years. In a recent publication in Nature (Y. Zhang et al, Nature, 372, 425–431, 1994) suggest that one of the molecules which plays a key role in energy balance regulation is the ob protein. Zhang et al also report the cloning and sequencing of both mouse and human ob gene protein.

To date there is no indication in the art as to the nature of the secondary or tertiary structural characteristics of the human or mouse ob protein. Zhang et al also report that the ob protein amino acid sequence has no significant homology with any sequence in Genbank.

It has now been indicated that the tertiary structure of the mouse and human ob proteins comprises a modified form of a four-helix bundle structure with an 'up-up, down-down' topology. In addition, novel molecules with the potential to mimic the physiological activity of the ob protein have been identified during investigations into the regions of the ob protein sequence which are indicated to interact with a putative receptor for this protein.

Such molecules have potential use in the treatment of nutritional and metabolic disorders, particularly obesity and diabetes in the case of agonists and anorexia and cachexia in the case of antagonists.

Accordingly, in a first aspect, the present invention provides a protein fragment of the ob protein, being an active site of said protein.

The active site is suitably provided by the ob protein when it is in the form of a four helix bundle structure, particularly that having an up-up down-down topology.

In particular, the active site is formed from one or more amino acids selected from one or more of the four helices forming the secondary structure of the ob protein, especially a protein fragment consisting of amino acid residues 26 to 39, 74 to 88, 93 to 113 or 142 to 161.

A suitable active site is formed from one or more amino acids selected from: R41, D30, T37, K26, T33, T40, R149, Q155, V145, Q151, S148,L158, W159, S73, Q84, Q77, V81, K74,S88,A80,T87, R105, S98, E102, I95, D106,N99 and H109 on the ob protein.

Hereinafter protein fragments of the ob protein will be referred to using an analogous abbreviation to the following: 'the protein fragment consisting of amino acid residues 26 to 39' is abbreviated to 'ob26–39'.

A suitable active site is formed from one or more amino acids selected from ob protein fragments ob26–39 and ob93–113.

A suitable active site is formed from one or more amino acids selected from ob protein fragments ob 74 –88 and ob142–161.

A suitable active site is formed from amino acids: R41, D30, T37, K26, T33, T40, R149, Q155, V145, Q151, L158 and W159 selected from the amino acid sequence of the human ob protein.

A suitable active site is formed from amino acids: S73, Q84, Q77, V81, K74, R105, S98, E102, I92, D106 and H109 selected from the amino acid sequence of the human ob protein.

A particular ob gene is the human ob gene.

Particular compounds with the potential to mimic the physiological activity of the ob protein are those formed by linking together amino acids selected from the above mentioned active sites. Accordingly, in a further aspect the invention provides a compound of formula (I):

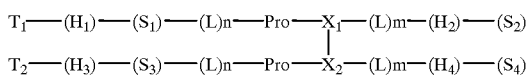

wherein:
$T_1$ and $T_2$ are optional N-terminator groups such as aliphatic acyl, ω-methoxy, α-oxycarbonyl or polyethylene glycol which may as further options be linked covalently to each other or incorporate moieties capable of targeting the construct to the blood-brain barrier such as fatty acid esters or phospholipids;
$S_1$, $S_2$, $S_3$ and $S_4$ are each linear peptide sequences of 10–30 aminoacids (preferably 12–20) which amino acids are selected from a sequentially contiguous residue from the amino acid sequence of a helix of the ob protein;
$H_1$, $H_2$, $H_3$ and $H_4$ each independently represents a bond or a linear sequence of 3–12 aminoacids;
(L)M and (L)N each independently comprise small hydrophilic aminoacid repeats, preferably of glycine or alanine. n and m being 1–8, preferably 2–4;
$X_1$ and $X_2$ are each either a bond, the aminoacid cysteine (in which case a disulphide bond forms the link between the sequence pairs), a homo- or heterobifunctional cross-linking agent (such as N,N'bis-maleimido diaminoalkane) so as to extend the length of the bridge within the range 2–20 atoms, preferably 2–8, or X represents glycine.

A particular helix of the ob protein is a protein fragment selected from ob26–39, ob74–88, ob93–113 or ob142–61.

Suitably, $S_1$, $S_2$, $S_3$ and $S_4$ represents a linear peptide sequences of amino acids selected from the sequentially contiguous residues of a helix of the ob protein, example include AKVQDDTKTLIKTIVTRI (SEQ ID NO: 1), SKM-DTLAVYQQILT (SEQ ID NO: 2), NVIQISNDLENL-RDLLHVLAFSK (SEQ ID NO: 3), and TEVVALSR-LLQGSLQDMLWQL (SEQ ID NO: 4).

Examples of H sequences include AK,AQ and LQ repeats. These sequences will be prepared as fusions such A-(Linker)-D and B-(Linker)-C and may be combined as (A–D)-(B–C) heterodimers or as homodimers such as (A–D)$_2$. Optionally, three helical sequences may be employed (e.g (A–B) - D).

In particular the invention includes the proteins having the sequence ID Nos set out below.

The invention also extends to the functional analogues, variants and derivatives of the proteins mentioned herein, including functional analogues, variants and derivatives of the peptide fragments and compound of formula (I).

Functional analogues includes functionally analogous proteins wherein one or more amino acids of the proteins mentioned herein are replaced with alternative amino acids.

Functional analogues also include small molecule agonists or antagonists of the compounds of formula (I) or the proteins mentioned herein, which may be identified and prepared by methods such as those disclosed in International patent application, publication number WO9605309.

Functional derivatives includes the proteins of the invention chemically modified by the attachment of groups or moieties so as to improve the physical properties, such as stability, or the therapeutic properties, for example the pharmaco kinetic properties, of the protein.

The peptides of the present invention may be prepared by conventional methods using liquid or solid-phase peptide peptide synthesis or by expression of DNA encoding such sequences in a suitable host. Preferably, that host will be bacterial, more preferably *Echerichia coli* K12.

Following synthesis or expression and purification by standard methods, the isolated peptides are coupled either directly molecular oxygen or other oxidising agents (homodimerisation) or by conversion on one component to a thiol-reactive form (for example a 2-pyridyldthio-derivative) for reaction with the free thiol form of the second component (heterodimerisation).

'Amino acid' is understood herein to mean naturally occurring L-amino acid. All representations of peptides herein follows the normal convention of N-terminal at the left and C-terminal at the right.

Peptide bonded units of the proteins associated with the present invention can be prepared by standard peptide synthesis techniques using a peptide synthesiser (Atherton, E. and Sheppard, R. C. (eds.) (1989) Solid Phase Peptide Synthesis: A practical approach, LRL Press, Oxford) followed by procedures appropriate to direct disulphide or amide bond formation.

Methods of well-known peptide synthesis are set forth by Ali et al., *J. Med. Chem.*, 29:984 (1986) and *J. Med. Chem.*, 30:2291 (1987) and are incorporated by reference herein. Preferably, the peptides are prepared by the solid phase technique of Merrifield (*J. Am. Chem. Soc.*, 85:2149 (1964)). However, a combination of solid phase and solution synthesis may be used, as in a convergent synthesis in which di-, tri-, tetra-, or penta-peptide fragments may be prepared by solid phase synthesis and either coupled or further modified by solution synthesis.

During synthesis, the side chain functional groups (e.g., —$NH_2$, —COOH, —OH, —SH) are protected during the coupling reactions. Normally, the a-amino group is temporarily protected as fluorenylmethoxycarbonyl (Fmoc) but other acid- or base-labile protecting groups can be used, e.g., t-Butoxycarbonyl (Boc). The amino side chain group of lysine is protected as t-butoxycarbonyl, benzyloxycarbonyl or p-chlorobenzyloxycarbonyl (Z or Cl—Z). Acetamidomethyl, trityl, t-butyl, S-t-butyl or para-methylbenzyl (p-MBz) protection is used for cysteines. Hydroxy groups are protected as butyl or benzyl ethers and carboxyl groups are protected as butyl, benzyl (Bz) or cyclohexyl esters.

The peptides can be synthesized either from the C-terminus or the N-terminus, preferably the former. Prior to coupling the alpha-carboxyl group (of a suitable protected amino acid) is activated. One skilled in the art can activate the protected group in a number of ways. For example, one may use N,N' dicyclohexylcarbodiimide (DCC), 2(1 H-benzotriazol- 1-yl)-1,1,3,3-tetramethyl uronium hexafluorophosphate (HBTU), p-nitrophenyl esters (pNp), hydroxybenzotriazole ester (HOBt), N-hydroxy succinimidyl ester (OSu) mixed anhydride or symmetrical anhydride.

Solution synthesis of peptides is accomplished using conventional methods to form amide bonds. Typically, a protected Boc-amino acid which has a free carboxyl group is coupled to a protected amino acid which has a free amino group using a suitable carbodiimide coupling agent, such as N,N' dicyclohexyl carbodiimide (DCC), optionally in the presence of 1-hydroxybenzotriazole (HOBT) and dimethylamino pyridine (DMAP).

In solution phase synthesis, the coupling reactions are preferably carried out at low temperature (e.g., −20° C.) in such solvents as dichloromethane (DCM), dimethyl formamide (DMF), N-methyl pyrrolidone (NMP), tetrahydrofuran (THF) acetonitrile (ACN) or dioxane.

If solid phase methods are used, the peptide is built up sequentially starting from the carboxy terminus and working towards the amino terminus of the peptide. Solid phase synthesis begins by covalently attaching the C terminus of a protected amino acid to a suitable resin, such as 4-(2',4'-dimethoxyphenyl-Fmoc-aminomethyl)-phenoxy resin (Rink amide resin, H. Rink, Tetrahedron Letters 28, 3787, (1987)), 4-benzyloxybenzyl alcohol resin (Wang resin, S. S. Wang, JACS, 95, 1328, (1973)) or 4-hydroxymethyl phenoxy acetic acid resin.

In the solid phase synthesis, the first amino acid residue is normally attached to an insoluble polymer. For example, two commonly used polymers are polystyrene (1% cross-linked with divinyl benzene) and 1% cross-linked polyacrylamide. These polymers are functionalised to contain a reactive group, e.g., —OH, —$NH_2$ and —$CH_2Cl$ to link the first amino acid of the targeted peptide (i.e., carboxy terminus). The choice of the linkage between the first amino acid and the polymer is dictated by the carboxy terminus of the peptide. For example, peptides having a carboxyl group at the C-terminus would be linked by an ester linkage and for peptides with a carboxamide ending would have an amide linkage.

Once the first protected amino acid has been coupled to the desired resin, the amino protecting group is removed by treatment with a secondary amine such as piperidine, and the free carboxyl of the next (protected) amino acid is coupled to this amino group. This process is carried out sequentially, without isolation of the intermediate, until the peptide of interest has been formed. The completed peptide may then be deblocked and/or cleaved from the resin in any order.

Preferred solvents for the coupling reactions include, but are not limited to, dichloromethane (DCM), dimethyl formamide (DMF) and N-methyl pyrrolidone (NMP). After the desired sequence is synthesised, the peptide is deprotected and cleaved from the resin using trifluoroacetic acid or trifluoromethane sulphonic acid.

The preferred method for cleaving a peptide from the support resin is to treat the resin supported peptide with trifluoroacetic acid in the presence of suitable cation and carbonium ion scavengers such as phenol, anisole, thioanisole, ethane dithiol, water or ethylmethyl sulphide.

To obtain the compounds of the present invention, the synthetic peptides may be cyclized/coupled using methods well known in the art.

For example coupling via a disulphide bond of two linear peptides both containing cysteine residues may be achieved in a selective manner by reaction of the free thiol on one chain with a suitably activated cysteine derivative on the other chain. A group which is especially useful as a displaceable protecting group is the S-(carbomethoxy-sulphenyl) derivative. Examplary of this method is the protection of both linear peptides' cysteine residues with the Acetamidomethyl (Acm) group. Treatment of one chain with mercury (II) acetate followed by beta mercaptoethanol removes the acetamidomethyl protecting group. Treatment of the second chain with carbomethoxysulphenyl chloride gives the activated species. Stirring of the two peptides in dilute aqueous solution at a pH of about 7 to 8 causes displacement of the carbomethoxysulphenyl group and formation of the interchain disulphide.

If an intramolecular disulphide is to be formed then the corresponding linear peptide can be completely deprotected and produced as a dimercaptan. Any oxidizing agent known in the art to be capable of converting a dimercaptan to a disulphide may then be used. Examplary of such agents are an alkali metal ferricyanide, (e.g., potassium or sodium ferricyanide), oxygen gas, diiodomethane or iodine. The reaction is conducted in a suitable inert solvent, such as aqueous methanol or water, at temperatures from about 0 to 40° C., under high dilution. The pH is usually maintained at about 7 to 8. Cyclisation may be performed upon the peptide while it is still attached to the support resin or while other functional groups are still protected, but it is preferably performed on the deprotected free peptide.

In cases where two disulphides are to be formed between two linear peptides, two types of cysteine thiol protecting groups can be employed eg Acm and trityl. Each peptide would contain one of each type arranged so that one pair of cysteines to be coupled are protected with trityl groups and the other pair with Acm. Independant removal of the trityl group from each peptide would give two separate monothiol derivatives which can be coupled by activating the thiol on one peptide with 2,2'dipyridyldisulphide and then adding the other monothiol peptide to give the bis(S-acetamidomethyl) disulphide-linked peptide. The second disulphide can be obtained by direct iodine oxidation of this product as described by Kamber (B. Kamber, Helv. Chim. Acta 54, 927, (1971)), and Kamber et. al. (B. Kamber et. al., Helv. Chim. Acta 63, 899, (1980)).

Peptide chains can also be coupled using a linking group such as —NH(CH$_2$)$_n$CO—. This is most easily achieved by employing the N$^\alpha$-Fmoc derivative of the corresponding amino acid (NH$_2$(CH$_2$)$_n$COOH) and incorporating it into the growing peptide chain during conventional solid phase synthesis. A similar strategy can be employed to couple peptide chains using the side chain carboxyl of an acidic amino acid such as glutamic acid, and the side chain amino of a basic amino acid such as lysine. In this case compounds such as the N$^6$-y glutamyllysine derivative below may be incorporated into the growing peptide chain during conventional solid phase synthesis

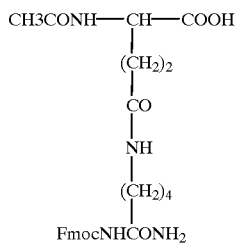

Coupling to the growing peptide chain is through the carboxyl of the glutamic acid residue and removal of the Fmoc grouping on the lysine a amino group provides a starting point for addition of further amino acids.

Alternatively the N$^\alpha$-trityl protecting group may be employed on the glutamic acid residue and after coupling this may be removed with 80% acetic acid and N-acetylated with acetic anhydride. Further couplings may proceed as previously described.

N-terminal N-acetyl groups may be introduced by acetylation of the free amino deprotected by removal of the amino protecting group, with acetic anhydride. C-terminal carboxamide groups are obtained by using an appropriate solid phase synthesis resin such as the Rink amide resin.

The functional analogues, variants and derivatives of the proteins mentioned herein may be prepared by using conventional methods analogous to those mentioned herein.

Salts include pharmaceutically acceptable salts, especially pharmaceutically acceptable acid addition salts.

Acid addition salts of the peptides are prepared in a standard manner in a suitable solvent from the parent compound and an excess of an acid, such as hydrochloric, hydrobromic, sulphuric, phosphoric, acetic, maleic, succinic, or methanesulphonic. The acetate salt form is especially useful. Certain of the compounds form inner-salts or zwitterons which may be acceptable. Cationic salts are prepared by treating the parent compound with an excess of an alkaline reagent, such as a hydroxide, carbonate or alkoxide containing the appropriate cation. Cations such as Na$^+$, K$^+$, Ca$^{2+}$ and NH$_4^+$ are examples of cations present in pharmaceutically acceptable salts.

Solvates include pharmaceutically acceptable solvates, such as hydrates.

The peptides can then be purified by a number of techniques. Preferred embodiments include gel filtration, reverse phase HPLC and crystallisation. More preferably, HPLC is used. The purified products can then be analysed for purity using HPLC, amino acid analysis, amino acid sequencing and fast atom bombardment mass spectrometry (FAB-MS).

Certain compounds of the invention which are single polypeptide chains may be prepared using recombinant DNA techniques by expression of DNA encoding the polypeptide sequence.

In a further aspect, the invention provides a process for preparing a compound according to the invention which process comprises expressing DNA encoding said compound in a recombinant host cell and recovering the product.

The DNA polymer comprising a nucleotide sequence that encodes the compound also forms part of the invention.

The process of the invention may be performed by conventional recombinant techniques such as described in Maniatis et. al., Molecular Cloning—A Laboratory Manual; Cold Spring Harbor, 1982 and DNA Cloning vols I, II and III (D. M. Glover ed., IRL Press Ltd).

In particular, the process may comprise the steps of:
i) preparing a replicable expression vector capable, in a host cell, of expressing a DNA polymer comprising a nucleotide sequence that encodes said compound;
ii) transforming a host cell with said vector;
iii) culturing said transformed host cell under conditions permitting expression of said DNA polymer to produce said compound; and
iv) recovering said compound.

The invention also provides a process for preparing the DNA polymer by the condensation of appropriate mono-, di- or oligomeric nucleotide units.

The preparation may be carried out chemically, enzymatically, or by a combination of the two methods,in vitro or in vivo as appropriate. Thus, the DNA polymer may be prepared by the enzymatic ligation of appropriate DNA fragments, by conventional methods such as those described by D. M. Roberts et al in Biochemistry 1985, 24, 5090–5098.

The DNA fragments may be obtained by digestion of DNA containing the required sequences of nucleotides with appropriate restriction enzymes, by chemical synthesis, by enzymatic polymerisation on DNA or RNA templates, or by a combination of these methods. Preferably total synthesis of DNA fragments would be employed.

Digestion with restriction enzymes may be performed in an appropriate buffer at a temperature of 20°–70° C., preferably in a volume of 50 ml or less with 0.1–10 mg DNA.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., preferably in a volume of 50 ml or less.

Enzymatic ligation of DNA fragments may be carried out using a DNA ligase such as T4 DNA ligase in an appropriate buffer at a temperature of 4° C. to ambient, preferably in a volume of 50 ml or less.

The chemical synthesis of the DNA polymer or fragments may be carried out by conventional phosphotriester, phosphite or phosphoramidite chemistry, using solid phase techniques such as those described in 'Chemical and Enzymatic Synthesis of Protein Fragments—A Laboratory Manual' (ed H. G. Gassen and A. Lang), Verlag Chemie, Weinheim (1982),or in other scientific publications, for example M. J. Gait, H. W. D. Matthes, M. Singh, B. S. Sproat, and R. C. Titmas, Nucleic Acids Research, 1982, 10, 6243; B. S. Sproat and W. Bannwarth, Tetrahedron Letters, 1983, 24, 5771; M. D. Matteucci and M. H. Caruthers, Tetrahedron Letters, 1980, 21, 719; M. D. Matteucci and M. H. Caruthers, Journal of the American Chemical Society, 1981, 103, 3185; S. P. Adams et al., Journal of the American Chemical Society, 1983, 105, 661; N. D. Sinha, J. Biemat, J. McMannus, and H. Koester, Nucleic Acids Research, 1984, 12, 4539; and H. W. D. Matthes et al., EMBO Journal, 1984, 3, 801. Preferably an automated DNA synthesizer is employed.

The DNA polymer is preferably prepared by ligating two or more DNA molecules which together comprise a DNA sequence encoding the compound.

The DNA molecules may be obtained by the digestion with suitable restriction enzymes of vectors carrying the required coding sequences.

The precise structure of the DNA molecules and the way in which they are obtained depends upon the structure of the desired product. The design of a suitable strategy for the construction of the DNA molecule coding for the compound is a routine matter for the skilled worker in the art.

The expression of the DNA polymer encoding the compound in a recombinant host cell may be carried out by means of a replicable expression vector capable, in the host cell, of expressing the DNA polymer. The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment, encode the compound, under ligating conditions.

The ligation of the linear segment and more than one DNA molecule may be carried out simultaneously or sequentially as desired.

Thus, the DNA polymer may be preformed or formed during the construction of the vector, as desired.

The choice of vector will be determined in part by the host cell, which may be prokaryotic, such as *E. Coli*, or eukaryotic, such as mouse C127, mouse myeloma, chinese hamster ovary, fungi e.g. filamentous fungi or unicellular yeast or an insect cell such as Drosophila. The host cell may also be in a transgenic animal. Suitable vectors include plasmids, bacteriophages, cosmids and recombinant viruses derived from, for example, baculoviruses or vaccinia.

The preparation of the replicable expression vector may be carried out conventionally with appropriate enzymes for restriction, polymerisation and ligation of the DNA, by procedures described in, for example, Maniatis et al., cited above. Polymerisation and ligation may be performed as described above for the preparation of the DNA polymer. Digestion with restriction enzymes may be performed in an appropriate buffer at a temperature of 20°–70° C., proteinrally in a volume of 50 ml or less with 0.1–10 mg DNA.

The recombinant host cell is prepared, in accordance with the invention, by transforming a host cell with a replicable expression vector of the invention under transforming conditions. Suitable transforming conditions are conventional and are described in, for example, Maniatis et. al., cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, Proc. Nat. Acad. Sci., 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells.

The invention also extends to a vector comprising a compound of the invention.

When used herein the term 'compound of the invention' includes the peptide (or protein) fragments mentioned herein, the compound of formula (I) mentioned herein; and the functional drivatives, variants and analogues thereof.

The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The expression product is recovered by conventional methods according to the host cell. Thus, where the host cell is bacterial, such as *E. coli* it may be lysed physically, chemically or enzymatically and the protein product isolated from the resulting lysate. If the product is to be secreted from the bacterial cell it may be recovered from the periplasmic space or the nutrient medium. Where the host cell is mammalian, the product may proteinrally be isolated from the nutrient medium The DNA polymer may be assembled into vectors designed for isolation of stable transformed mammalian cell lines expressing the product; e.g. bovine papillomavirus vectors or amplified vectors in chinese hamster ovary cells (DNA cloning Vol.II D. M. Glover ed. IRL Press 1985; Kaufman, R. J. et al., Molecular and Cellular Biology 5, 1750–1759, 1985; Pavlakis G. N. and Hamer, D. H., Proceedings of the National Academy of Sciences (USA) 80, 397–401, 1983; Goeddel, D. V. et al., European Patent Application No. 0093619, 1983).

As stated, the compounds of the invention and the salts and/or solvates thereof are indicated to have useful pharmaceutical properties. Accordingly, there is also provided a compound of the invention for use as an active therapeutic substance.

In particular the compounds of the invention are considered to be capable of regulating the physiological activity of the ob protein and are therefore of potential use in the treatment of nutritional and metabolic disorders, particularly obesity and diabetes in the case of agonists and anorexia and cachexia in the case of antagonists.

The invention also provides a method for the treatment of nutritional and metabolic disorders, which method comprises the administration of a compound of the invention or a salt and/or solvate thereof.

The invention therefore further provides a pharmaceutical composition comprising a compound of the invention or a salt and/or solvate thereof and a pharmaceutically acceptable carrier.

In use the active compound will normally be employed in the form of a pharmaceutical composition in association with a human or veterinary pharmaceutical carrier, diluent and/or excipient, although the exact form of the composition will depend on the mode of administration. The active compound may, for example, be employed in the form of tablets, capsules, lozenges or syrups for oral administration; in the form of snuff, aerosol or nebulisable solution for inhalation; in the form of sterile solutions for parenteral administration, or in the form of creams, lotions, liniments, gels, ointments or sprays for topical administration. Parenteral routes of administration include intravenous, intramuscular, subcutaneous, transcutaneous and intraperitoneal adminstration.

Also included are formulations of the above derivatives suitable for use in subcutaneously implanted pumps or controlled release devices, in transdermal patches and as micronised powders suitable for intranasal administration.

The dosage ranges for administration of the compounds of the present invention are those to produce the desired effect on the condition to be treated, the dosage will proteinrally vary with age, extent or severity of the medical condition and contraindications, if any. The dosage can vary from 0.001 mg/kg/day to 50 mg/kg/day, but preferably 0.01 to 1.0 mg/kg/day.

Solid oral dosage forms may contain conventional excipients such as diluents, for example lactose, microcrystalline cellulose, dicalcium phosphate, mannitol, magnesium carbonate, glycine, dextrose, sucrose, starch, sorbitol and calcium carbonate; binders, for example liquid glucose, syrup, acacia, gelatin, starch mucilage, methylcellulose, polyvinylpyrrolidone, alginates, and pregelatinised starch; disintegrants for example starch, alginic acid, microcrystalline cellulose, pectin, cross-linked polyvinylpyrrolidone, sodium starch glycollate and sodium carboxymethylcellulose; glidants for example talc and silica; lubricants for example stearic acid and magnesium stearate; preservatives for example sorbic acid and methyl or propyl parahydroxybenzoate, or pharmaceutically acceptable wetting agents for example sodium lauryl sulphate.

Capsules consist of a shell, normally of gelatin together with other ingredients for example, glycerol, sorbitol, surface-active agents, opaque fillers, preservatives, sweeteners, flavours and colours. The contents of capsules may include diluents, lubricants and disintegrants. Tablets consist of compressed powders or granules, may be coated or uncoated and may be designed so as to dissolve, disperse or effervesce before administration to the patient, or to dissolve or disperse in the gastrointestinal tract either immediately after swallowing, or, for example in the case of tablets with acid-insoluble coatings, at later times. Tablets usually contain excipients such as diluents, binders, disintegrants, glidants, lubricants and may contain colours and flavours. Effervescent tablets preferably contain acids together with carbonates or bicarbonates. Coatings for tablets may consist of natural or synthetic resins, gums, insoluble fillers, sugars, plasticisers, polyhydric alcohols and waxes and may also contain colours and flavours. Lozenges and pastilles are intended to dissolve in the mouth. Lozenges may be moulded or compressed, and usually have a flavoured base. Pastilles are moulded from a base of gelatin and glycerol or acacia and sucrose. They may contain a preservative as well as colours and flavours.

Film-coating resins include cellulose derivatives, zein, vinyl polymers and acrylic resins, and coating compositions usually include plasticisers, such as castor oil or glycerol triacetate. Enteric-coating resins include cellulose acetate phthalate and copolymers of methacrylic acid.

Solid compositions suitable for oral administration may be obtained by conventional methods of blending, filling, granulation, tabletting or the like. Repeated blending operations may be used to distribute the active agent throughout those compositions employing large quantities of fillers.

Liquid compositions suitable for oral administration may be in the form of, for example, elixirs, mixtures, concentrated solutions, suspensions, emulsions or linctuses. They may be presented as a dry product for reconstitution with water or other suitable vehicle before use. Such liquid compositions may contain conventional excipients such as suspending agents, for example sucrose, sorbitol, gelatin, methyl cellulose, carboxymethylcellulose, hydroxypropyl methyl cellulose, sodium alginate, Xanthan gum, acacia, carageenan, silica, aluminium stearate gel; emulsifying agents, for example lecithin, acacia, sorbitan mono-oleate; aqueous or non-aqueous vehicles which include edible oils, oily esters, for example esters of glycerol, ethanol, glycerol; buffering agents for example citrates and phosphates of alkali metals; preservatives, for example sodium benzoate, sorbic acid, methyl or propyl parahydroxybenzoate; and if desired, conventional flavouring and colouring agents.

The composition may be implanted subcutaneously, for example in the form of a compressed tablet or slow release capsule.

Alternatively, compositions suitable for injection may be in the form of solutions, suspensions or emulsions, or dry powders which are dissolved or suspended in a suitable vehicle prior to use.

Fluid unit dosage forms are prepared utilising the compound and a pyrogen-free sterile vehicle. The compound, depending on the vehicle and concentration used, can be either dissolved or suspended in the vehicle. Solutions may be used for all forms of parenteral administration, and are particularly used for intravenous infection. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area. Alternatively the drug and other ingredients may be dissolved in an aqueous vehicle, the solution is sterilised by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile compound is suspended in the sterile vehicle, instead of being dissolved and sterilisation cannot be accomplished by filtration. The compound may be isolated in a sterile state or alternatively it may be sterilised after isolation, e.g. by gamma irradiation. Advantageously, a suspending agent for example polyvinylpyrrolidone is included in the composition to facilitate uniform distribution of the compound.

In a further aspect there is provided a method of treating nutritional and metabolic disorders, such as obesity and diabetes or anorexia and cachexia, which comprises administering to the sufferer an effective, non-toxic amount of a compound of the invention or a salt and/or solvate thereof.

The invention further provides a compound of the invention or a salt and/or solvate thereof for use as an active therapeutic substance, in particular for use in treating nutritional and metabolic disorders, such as obesity and diabetes or anorexia and cachexia.

The invention also provides the use of a compound of the invention or a salt and/or solvate thereof in the manufacture of a medicament for treating nutritional and metabolic disorders, such as obesity and diabetes or anorexia and cachexia.

No unexpected toxicological effects are expected when compounds of the invention are administered in accordance with the present invention.

The following examples illustrate compounds of the invention.

The following compounds are prepared according to the methods disclosed herein.

Pharmacological Methods: The activity of the compounds of the invention are assessed according to the methodology set our below:

Effect of peptide derivatives on body weight and food intake in SD rats.

Male Sprague-Dawley rats (240–250 g body weight) supplied by Charles River (UK). Animals are maintained on 12 h light and 12 h dark cycle at a laboratory temperature of $22\pm2°$ C. and given free access to standard rat chow and water. After 5–7 days of adaptation to the Animal Unit conditions, the animals are implanted with a lateral brain ventricle cannula.

Surgery: Rats are pre-treated with synulox (0.1 ml/100 g) approximately 1 h before anaesthesia. Then animals are anaesthetised with domitor (0.04 ml/100 g, i.m.) and sublimase (0.9 mil/100 g, i.p.). Each rat has a cannula implanted stereotaxically into the lateral ventricle under sterile conditions. Anaesthesia is reversed using antisedan and nubain (50% v/v:50% v/v 0.02 ml/100 g, i.p.). Following surgery body weight is monitored daily. After 3 days recovery, rats are housed in experimental cages. To check the placement of the cannula in the lateral ventricle, angiotensin II (100 ng/5 ul) is injected intracerebroventricularly (icv) and water intake is monitored (5 min after injection). After 6 days from surgery, animals are divided into two groups (8 rats per group) according to their body weight. Body weights are recorded daily at 9.0 a.m. On day 6 after surgery, food is withdrawn from all animals at 9.0 a.m. On day 7, rats are weighed and injected icv at 9 a.m. with either vehicle (5 $\mu$l/rat) or peptide derivative (1 nM-1 $\mu$M/5 $\mu$l ), then supplied with food. 24 h food intake and body weight is recorded.

EXAMPLE 1:

Ac-AKVQDDTKTLIKTIVTRIGGPCGSGTEVVALSRLLQGSLQDMLWQL-OH    (SEQ ID NO: 5)
                          |
                          S
                          |
                          S
                          |
Ac-ASKMDQTLAVYQQILTGSAAPCGGNVIQISNDLENLRDLLHVLAFSK-OH    (SEQ ID NO: 6).

EXAMPLE 2:

MeO-PEG$_{4000}$-CO-AKNVIQISNDLENLRDLLHVLAFSKAAPC    (SEQ ID NO: 7)
                              |
                              S
                              |
                              S
                              |
MethoxyPEG$_{4000}$-CO-AKVQDDTKTLIKTIVTRIAAPCGGSTEVVALSRLLQGSLQDMLWQL-OH    (SEQ ID NO: 8)

What is claimed is:

1. An isolated ob protein fragment consisting of amino acid residues 26 to 39, 74 to 88, 93 to 113 or 142 to 161 of the ob protein.

2. A compound of formula (I):

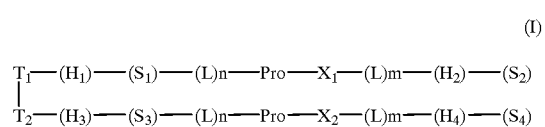

wherein:

$T_1$ and $T_2$ are optional N-terminator groups;

$S_1$, $S_2$, $S_3$ and $S_4$ are each linear peptide sequences of 10–30 amino acids of an ob protein helix;

$H_1$, $H_2$, $H_3$ and $H_4$ each independently represents a bond or a linear sequence of 3–12 amino acids;

each of (L)n and (L)m is a small hydrophilic amino acid repeat, n and m are 1–8; and $X_1$ and $X_2$ are each either a bond, cysteine, glycine or $X_1$–$X_2$ is a homo- or heterobifunctional cross-linking agent.

3. The compound of claim 2 wherein $T_1$ and $T_2$ are linked covalently to each other or incorporate moieties capable of targeting the blood-brain barrier.

4. The compound of claim 2 wherein $S_1$, $S_2$, $S_3$ and $S_4$ are 12–20 amino acids.

5. The compound of claim 4 wherein $S_1$, $S_2$, $S_3$ and $S_4$ represent a linear amino acid sequence selected from sequentially contiguous residues of an ob protein helix.

6. The compound of claim 5 wherein $S_1$, $S_2$, $S_3$ and $S_4$ are selected from the group consisting of AKVQDDTKTLIK-TIVTRI (SEQ ID NO: 1), SKMDTLAVYQQILT (SEQ ID NO: 2), NVIQISNDLENLRDLLHVLAFSK (SEQ ID NO: 3) and TEVVALSRLLQGSLQDMLWQL (SEQ ID NO: 4).

7. The compound of claim 2 wherein $L_1$, $L_2$, $L_3$ and $L_4$ are glycine or alanine and n and m are 2–4.

8. The compound of claim 2 wherein $X_1$–$X_2$ is a homo- or heterobifunctional cross-linking agent with a length range of 2–20 atoms.

9. The compound of claim 8 wherein the cross-linking agent is N,N' bis-maleimido diaminoalkane and the length range is 2–8 atoms.

10. The compound

11. The compound

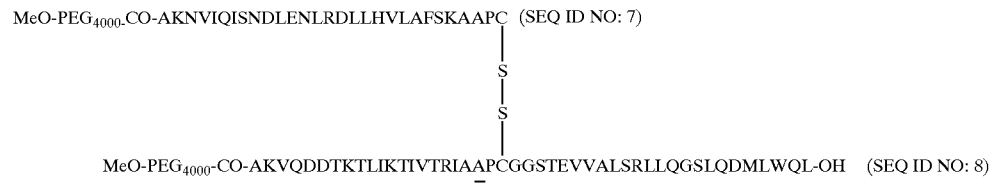

12. A process for preparing the compound of claim 2 comprising:
  i) preparing a replicable expression vector capable, in a host cell, of expressing a DNA polymer comprising a nucleotide sequence that encodes the compound;
  ii) transforming a host cell with the vector;
  iii) culturing the transformed host cell under conditions permitting expression of the DNA polymer to produce the compound; and
  iv) recovering the compound.

13. A pharmaceutical composition comprising the compound of claim 2, or a salt and/or solvate thereof, and a pharmaceutically acceptable carrier.

14. A method of treating nutritional or metabolic disorders comprising administering the compound of claim 2 to a sufferer.

15. The method of claim 14 wherein the disorders are selected from the group consisting of obesity and diabetes.

16. The compound of claim 2 wherein $T_1$ and $T_2$ are aliphatic acyl, $\omega$-methoxy, $\alpha$-oxycarbonyl or polyethylene glycol.

17. The compound of claim 3 wherein the moieties capable of targeting the blood-brain barrier are fatty acid esters or phospholipids.

* * * * *